(12) United States Patent
Quadling et al.

(10) Patent No.: US 7,342,668 B2
(45) Date of Patent: Mar. 11, 2008

(54) HIGH SPEED MULTIPLE LINE THREE-DIMENSIONAL DIGITALIZATION

(75) Inventors: Mark Quadling, Plano, TX (US); Henley Quadling, Addison, TX (US)

(73) Assignee: D4D Technologies, LLC, Richardson, TX (US)

( * ) Notice: Subject to any disclaimer, the term of this patent is extended or adjusted under 35 U.S.C. 154(b) by 411 days.

(21) Appl. No.: 10/943,273

(22) Filed: Sep. 17, 2004

(65) Prior Publication Data

US 2005/0099638 A1    May 12, 2005

Related U.S. Application Data (60) Provisional application No. 60/503,666, filed on Sep. 17, 2003.

(51) Int. Cl.
*G01B 11/24* (2006.01)
*G06K 9/00* (2006.01)

(52) U.S. Cl. .......................... 356/603; 382/154

(58) Field of Classification Search ........ 356/601–614; 382/6, 34, 154, 284; 433/215, 218, 223, 433/31, 37
See application file for complete search history.

(56) References Cited

U.S. PATENT DOCUMENTS

| | | | |
|---|---|---|---|
| 4,411,626 A | 10/1983 | Becker et al. | |
| 4,478,580 A | 10/1984 | Barrut | |
| 4,486,842 A * | 12/1984 | Hermann | 700/259 |
| 4,575,805 A | 3/1986 | Moermann et al. | |
| 4,611,288 A | 9/1986 | Duret et al. | |
| 4,615,678 A | 10/1986 | Moermann et al. | |
| 4,663,720 A | 5/1987 | Duret et al. | |
| 4,687,326 A * | 8/1987 | Corby, Jr. | 356/5.01 |
| 4,742,464 A | 5/1988 | Duret et al. | |
| 4,752,964 A | 6/1988 | Okada et al. | |
| 4,766,704 A | 8/1988 | Brandestini et al. | |
| 4,798,534 A | 1/1989 | Breads | |
| 4,816,920 A | 3/1989 | Paulsen | |
| 4,837,732 A * | 6/1989 | Brandestini et al. | 433/29 |
| 4,856,991 A | 8/1989 | Breads et al. | |
| 4,935,635 A | 6/1990 | O'Harra | |
| 4,936,862 A | 6/1990 | Walker et al. | |
| 4,952,149 A | 8/1990 | Duret et al. | |
| 4,964,770 A | 10/1990 | Steinbichler et al. | |
| 4,970,032 A | 11/1990 | Rotsaert | |
| 5,027,281 A | 6/1991 | Rekow et al. | |
| 5,035,613 A | 7/1991 | Breads et al. | |
| 5,055,039 A | 10/1991 | Abbatte et al. | |

(Continued)

FOREIGN PATENT DOCUMENTS

EP    0 600 800 A1    6/1994

OTHER PUBLICATIONS

Baumgartner, A., "Polarization-Sensitive Optical Coherence Tomography of Dental Structures", *Caries Res.*, vol. 34, 2000, pp. 59-69.

(Continued)

*Primary Examiner*—Sang H. Nguyen
(74) *Attorney, Agent, or Firm*—David H. Judson (57) ABSTRACT

A system provides high-speed multiple line digitization for three-dimensional imaging of a physical object. A full frame of three-dimensional data may be acquired in the same order as the frame rate of a digital camera.

22 Claims, 7 Drawing Sheets

U.S. PATENT DOCUMENTS

| | | |
|---|---|---|
| 5,059,118 A | 10/1991 | Breads et al. |
| 5,092,022 A | 3/1992 | Duret |
| 5,106,303 A | 4/1992 | Oden et al. |
| 5,139,419 A | 8/1992 | Andreiko et al. |
| 5,151,044 A | 9/1992 | Rotsaert |
| 5,186,623 A | 2/1993 | Breads et al. |
| 5,224,049 A | 6/1993 | Mushabac |
| 5,257,184 A | 10/1993 | Mushabac |
| 5,266,030 A | 11/1993 | Van Der Zel |
| 5,273,429 A | 12/1993 | Rekow et al. |
| 5,338,198 A | 8/1994 | Wu et al. |
| 5,340,309 A | 8/1994 | Robertson |
| 5,342,202 A | 8/1994 | Deshayes |
| 5,342,696 A | 8/1994 | Eidenbenz et al. |
| 5,347,454 A | 9/1994 | Mushabac |
| 5,368,478 A | 11/1994 | Andreiko et al. |
| 5,372,502 A | 12/1994 | Massen et al. |
| 5,378,154 A | 1/1995 | Van Der Zel |
| 5,382,164 A | 1/1995 | Stern |
| 5,383,752 A | 1/1995 | Rheinberger et al. |
| 5,386,292 A | 1/1995 | Massen et al. |
| 5,395,238 A | 3/1995 | Andreiko et al. |
| 5,417,572 A | 5/1995 | Kawai et al. |
| 5,431,562 A | 7/1995 | Andreiko et al. |
| 5,440,393 A | 8/1995 | Wenz |
| 5,440,496 A | 8/1995 | Andersson et al. |
| 5,447,432 A | 9/1995 | Andreiko et al. |
| 5,448,472 A | 9/1995 | Mushabac |
| 5,452,219 A | 9/1995 | Dehoff et al. |
| 5,454,717 A | 10/1995 | Andreiko et al. |
| 5,474,448 A | 12/1995 | Andreiko et al. |
| RE35,169 E | 3/1996 | Lemchen et al. |
| 5,497,336 A | 3/1996 | Andersson et al. |
| 5,533,895 A | 7/1996 | Andreiko et al. |
| 5,545,039 A | 8/1996 | Mushabac |
| 5,549,476 A | 8/1996 | Stern |
| 5,562,448 A | 10/1996 | Mushabac |
| 5,569,578 A | 10/1996 | Mushabac |
| 5,587,912 A | 12/1996 | Andersson et al. |
| 5,604,817 A * | 2/1997 | Massen et al. ............... 382/120 |
| 5,607,305 A | 3/1997 | Andersson et al. |
| 5,652,709 A | 7/1997 | Andersson et al. |
| 5,683,243 A | 11/1997 | Andreiko et al. |
| 5,691,905 A | 11/1997 | Dehoff et al. |
| 5,725,376 A | 3/1998 | Poirier |
| RE35,816 E | 6/1998 | Schulz |
| 5,788,498 A | 8/1998 | Wohlwind |
| 5,800,174 A | 9/1998 | Andersson |
| 5,812,269 A | 9/1998 | Svetkoff et al. |
| 5,813,859 A | 9/1998 | Hajjar et al. |
| 5,818,587 A | 10/1998 | Devaraj et al. |
| 5,823,778 A | 10/1998 | Schmitt et al. |
| 5,851,115 A | 12/1998 | Carlsson et al. |
| 5,857,853 A | 1/1999 | Van Nifterick et al. |
| 5,870,220 A | 2/1999 | Migdal et al. |
| 5,879,158 A | 3/1999 | Doyle et al. |
| 5,880,962 A | 3/1999 | Andersson et al. |
| 5,882,192 A | 3/1999 | Bergersen |
| 5,938,446 A | 8/1999 | Andersson et al. |
| 5,975,893 A | 11/1999 | Chishti et al. |
| 6,015,289 A | 1/2000 | Andreiko et al. |
| 6,044,170 A | 3/2000 | Migdal et al. |
| 6,049,743 A | 4/2000 | Baba |
| 6,062,861 A | 5/2000 | Anderson |
| 6,068,482 A | 5/2000 | Snow |
| 6,099,314 A | 8/2000 | Kopelman et al. |
| 6,102,696 A * | 8/2000 | Osterwalder et al. ......... 433/29 |
| 6,115,114 A | 9/2000 | Berg et al. |
| 6,135,774 A | 10/2000 | Hack et al. |
| 6,152,731 A | 11/2000 | Jordan et al. |
| 6,200,135 B1 | 3/2001 | Hultgren |
| 6,205,240 B1 | 3/2001 | Pietrzak et al. |
| 6,206,693 B1 | 3/2001 | Hultgren |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,227,851 B1 | 5/2001 | Chishti et al. |
| 6,244,861 B1 | 6/2001 | Andreiko et al. |
| 6,250,918 B1 | 6/2001 | Sachdeva et al. |
| 6,287,119 B1 | 9/2001 | van Nifterick et al. |
| 6,287,121 B1 | 9/2001 | Guiot et al. |
| 6,315,553 B1 | 11/2001 | Sachdeva et al. |
| 6,318,995 B1 | 11/2001 | Sachdeva et al. |
| 6,322,359 B1 | 11/2001 | Jordan et al. |
| 6,334,773 B1 * | 1/2002 | Ahlen et al. .................. 433/29 |
| 6,350,120 B1 | 2/2002 | Sachdeva et al. |
| 6,359,680 B1 | 3/2002 | Rubbert |
| 6,364,660 B1 | 4/2002 | Durbin et al. |
| 6,382,975 B1 | 5/2002 | Poirier |
| 6,386,867 B1 | 5/2002 | Durbin et al. |
| 6,386,878 B1 | 5/2002 | Pavlovskaia et al. |
| 6,394,801 B2 | 5/2002 | Chishti et al. |
| 6,398,548 B1 | 6/2002 | Muhammad et al. |
| 6,398,554 B1 | 6/2002 | Perot et al. |
| 6,402,707 B1 | 6/2002 | Ernst |
| 6,406,292 B1 | 6/2002 | Chishti et al. |
| 6,409,504 B1 | 6/2002 | Jones et al. |
| 6,413,084 B1 | 7/2002 | Rubbert et al. |
| 6,414,708 B1 * | 7/2002 | Carmeli et al. ............... 348/42 |
| 6,431,870 B1 | 8/2002 | Sachdeva |
| 6,431,871 B1 * | 8/2002 | Luthardt ..................... 433/223 |
| 6,457,972 B1 | 10/2002 | Chishti et al. |
| 6,463,344 B1 | 10/2002 | Pavlovskaia et al. |
| 6,464,496 B1 | 10/2002 | Sachdeva et al. |
| 6,471,512 B1 | 10/2002 | Sachdeva et al. |
| 6,482,284 B1 | 11/2002 | Reidt et al. |
| 6,497,574 B1 | 12/2002 | Miller |
| 6,499,997 B2 | 12/2002 | Chishti et al. |
| 6,506,054 B2 | 1/2003 | Shoher et al. |
| 6,512,994 B1 | 1/2003 | Sachdeva |
| 6,514,074 B1 | 2/2003 | Chishti et al. |
| 6,532,299 B1 | 3/2003 | Sachdeva et al. |
| 6,540,512 B1 | 4/2003 | Sachdeva et al. |
| 6,554,611 B2 | 4/2003 | Chishti et al. |
| 6,554,613 B1 | 4/2003 | Sachdeva et al. |
| 6,568,936 B2 | 5/2003 | MacDougald et al. |
| 6,594,539 B1 * | 7/2003 | Geng ........................ 700/117 |
| 2002/0143506 A1 | 10/2002 | D'Aligny et al. |
| 2003/0045798 A1 | 3/2003 | Hular et al. |

OTHER PUBLICATIONS

Otis, Lind et al., "Identification of Occlusal Sealants Using Optical Coherence Tomography", *J. Clin. Den.*, vol. XIV, No. 1, 2003, pp. 7-10.

Otis, Linda et al., "Optical Coherence Tomography: A New Imaging Technology for Dentistry", *JADA*, vol. 131, 2000, pp. 511-514.

International Search Report for corresponding PCT application No. PCT/US03/41701, dated Jun. 4, 2004, 4 pages.

* cited by examiner

HIGH SPEED MULTIPLE LINE THREE-DIMENSIONAL DIGITALIZATION

PRIORITY AND CROSS REFERENCE TO RELATED APPLICATION

This application claims the benefit under 35 U.S.C. § 119(e) of co-pending provisional application No. 60/503,666 filed Sep. 17, 2003 for High Speed Multiple Line Three-Dimensional Digitization, which is incorporated in its entirety herein by reference.

BACKGROUND OF THE INVENTION

1. Technical Field

This invention generally relates to three-dimensional imaging of a physical object, and in particular to a high-speed multi-line triangulation for three-dimensional digitization of a physical object.

2. Related Art

Imaging techniques provide a three-dimensional visualization of a physical object on a video terminal or monitor. The three-dimensional visualization may illustrate surface characteristics of the physical object. Data associated with the surface characteristics are generated and processed by a processor to generate the three-dimensional visualization.

Data associated with the surface characteristics are generated by capturing images of the object from various perspectives. The perspectives are mapped or combined to produce a set of data points that represent the various surfaces of the object. The data points are processed to generate the three-dimensional visual display of the object. The data points also may be processed to represent the object in a dimensionally correct manner in the computer. However, the time to generate the data points is longer than the display rate for the digital camera.

Imaging systems that use a triangulation technique emanate a single point or a single line on the object to determine relative surface characteristics of the object. Multiple line systems are limited by the maximum number of simultaneous lines that may image the object and require a large number of images to obtain a final image of the object.

A Moiré technique may use multiple lines to compute a relative height map of the surface characteristics. Each point has a known or predetermined relative relationship to a neighboring point on a neighboring line. A sinusoidal variation of the lines provides a trigonometric solution to estimate the relative relationships or equivalently extracting the phase. Such technique requires either multiple images or substantial processing time to provide a three-dimensional image.

Accordingly, there is a need for a high-speed three dimensional imaging system that minimizes the number of images and amount of computation to provide a three-dimensional image.

SUMMARY

By way of introduction only, a high speed multiple line three-dimensional digitization may include imaging a physical object to provide a visualization or virtualization of the object that may be viewed and manipulated by using a processor. The high speed multiple line three-dimensional digitization may be achieved by one or more apparatuses, devices, systems, methods, and/or processes.

In an embodiment, the high-speed multiple-line digitization generates a full frame of three-dimensional data of a surface of a physical object that is acquired in substantially the same order as a frame rate of a camera used to acquire or capture the three-dimensional image. For example, a camera used to capture a three-dimensional image has a frame rate of N frames per second. A full frame of three-dimensional data is obtained in a time frame of m/N seconds where m different patterns are projected. For example, where two patterns are projected, a full frame of three-dimensional data is obtained in a time frame f 2/N seconds. The full frame of three-dimensional data includes multiple data points represented by multiple floating point numbers.

The foregoing summary is provided only by way of introduction. The features and advantages of the high speed multiple line three-dimensional digitization may be realized and obtained by means of the instrumentalities and combinations particularly pointed out in the claims. Nothing in this section should be taken as a limitation on the claims, which define the scope of the invention. Additional features and advantages of the present invention will be set forth in the description that follows, and in part will be obvious from the description, or may be learned by practice of the present invention.

BRIEF DESCRIPTION OF THE DRAWINGS

The invention can be better understood with reference to the following drawings and description. The components in the figures are not necessarily to scale, emphasis instead being placed upon illustrating principles of the invention. Moreover, in the figures, like referenced numerals designate corresponding parts throughout the different views.

DETAILED DESCRIPTION OF THE PREFERRED EMBODIMENTS

Hereinafter exemplary embodiments are discussed with reference to accompanied figures.

Figure 1:
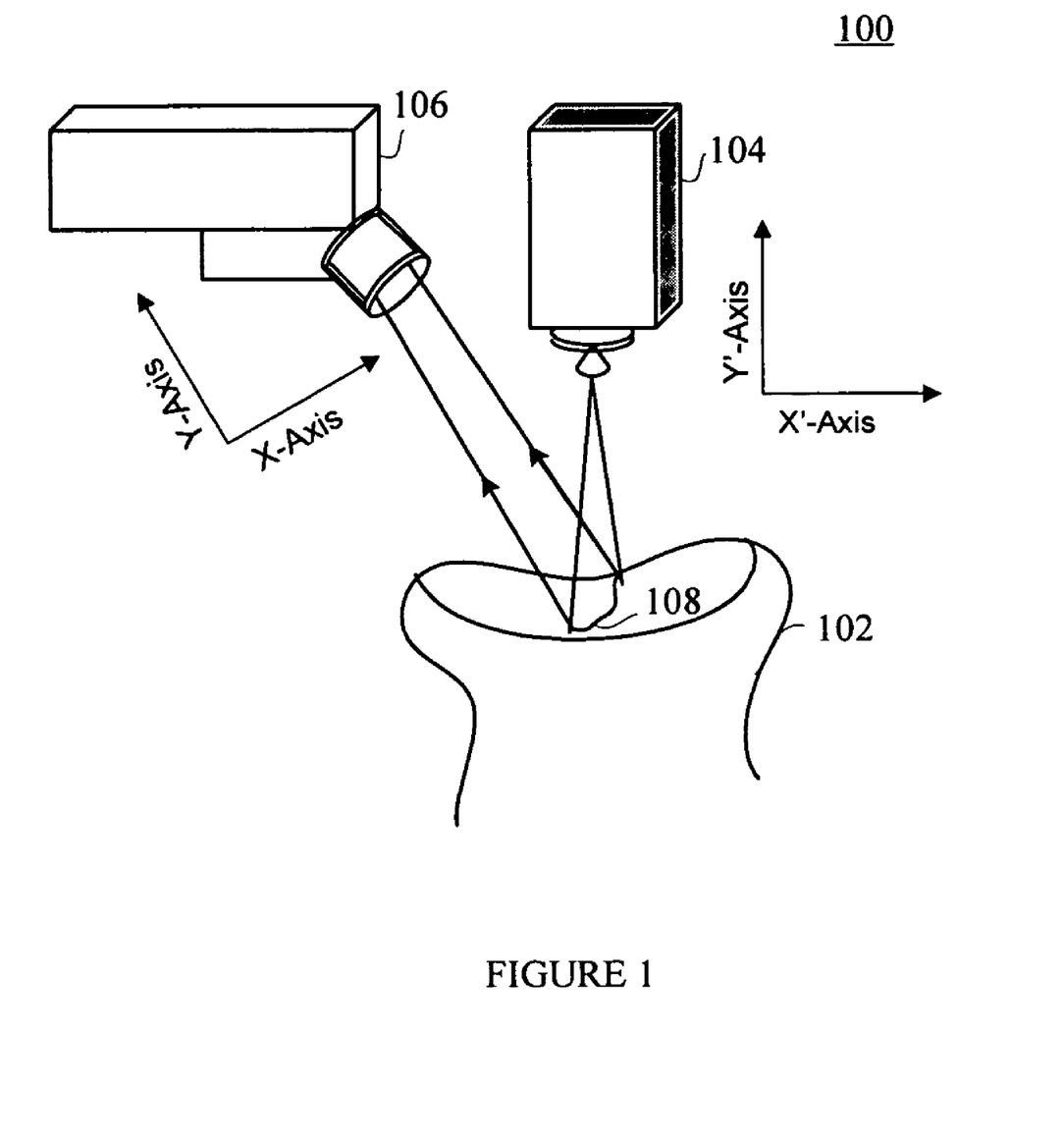
FIG. 1 illustrates a high-speed multi-line three-dimensional digitization system having a camera fixed relative to a line projector.

FIG. 1 illustrates a digitization system 100. The digitization system 100 includes a camera 106 and a line pattern projector or illuminator 104. The camera 106 is fixed relative to the line pattern projector 104. The projector 104 illuminates a portion of a surface 108 of object 102 with a light pattern. The object may be any physical object capable of being imaged. In an embodiment, the object may be dentition or dental items including molds, castings, dentition, prepared dentition and the like.

Light reflected from the surface 108 is captured by the camera 106. Based on the reflected light pattern, three-dimensional data representative of the illuminated surface 108 may be generated. The three-dimensional data may be processed to generate a three-dimensional image of the illuminated surface 108. The camera 106 may be characterized by a local coordinate system XY, and the projector 104 characterized by a local coordinate system X'Y'.

Figure 2:
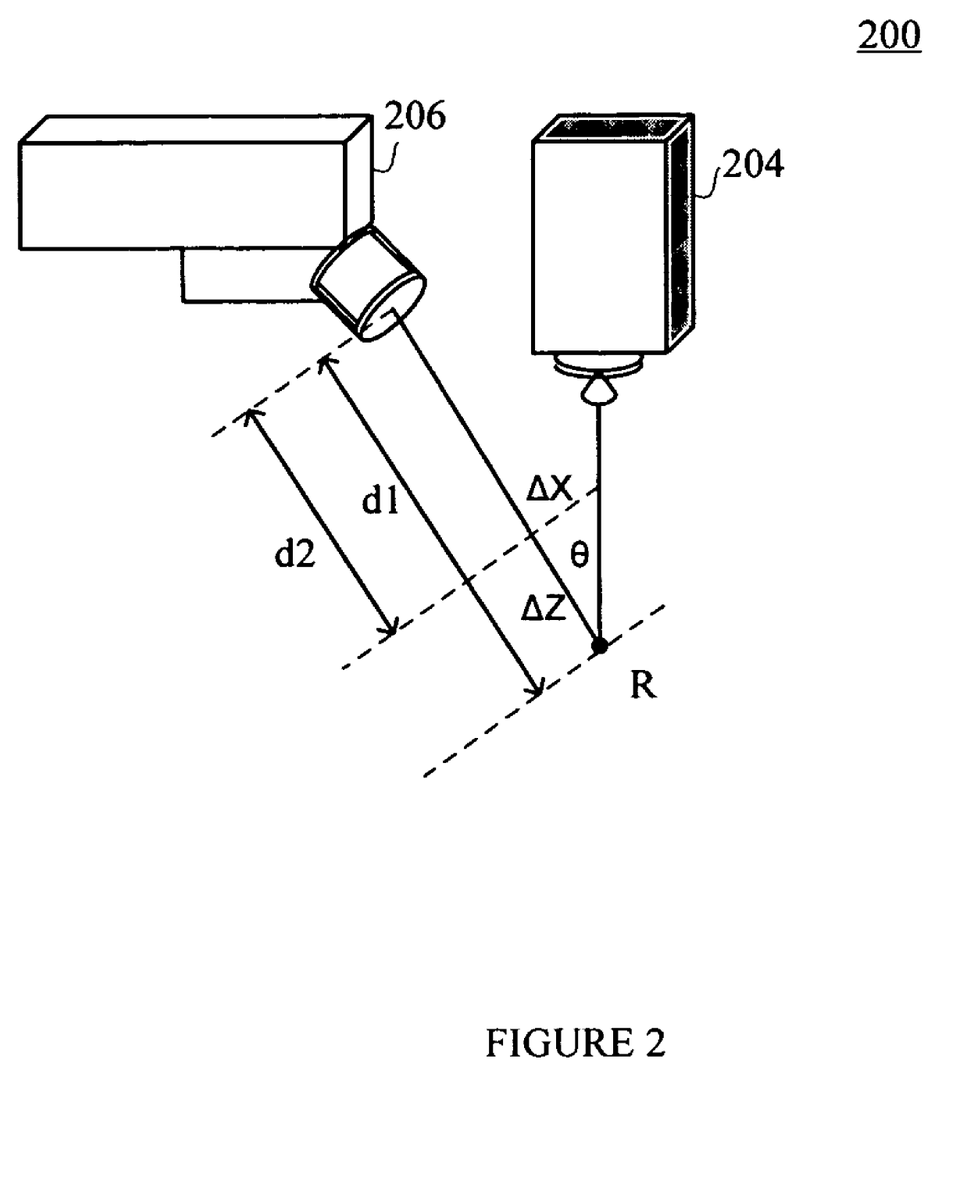
FIG. 2 illustrates a coordinate view of the system of FIG. 1.

Referring to FIG. 2, pattern projector 204 projects a pattern during a capture or read period. The pattern may be considered to be an assembly of multiple points. The number of points may be finite or substantially infinite. The size of the points may be finite or infinitesimal. An example of such a pattern is a pattern consisting of multiple lines. The pattern may be structured white light.

In an embodiment, camera 206 is a high-speed camera that images general patterns or multiple line patterns. The camera 206 may also capture multiple line patterns during a read period. The relationship shown in FIG. 2 refers to a single point in such a line pattern. A triangulation axis R may be defined as passing through an intersection of an axial ray from camera 206 and an axial ray of projector 204. The axis R may be perpendicular to an axial ray from camera 206 and an axial ray of projector 204. The triangulation axis R also may be substantially parallel to Y and Y'. A minimum angle θ between a valid ray between the projector 204 relative to a valid axial ray of the camera 206 is non-zero.

A line projected by projector 204 represents a connected series of points or curvilinear segments where a normal vector n at any point along the curve obeys the following equation or rule:

$$|n \cdot R| \geq \frac{1}{\sqrt{2}} \quad (1)$$

According to Equation (1), the angle between a point on the curve and the triangulation axis R is greater than or equal to about 45 degrees. The line may have a cross-sectional intensity characterized by a function that is independent of Equation 1. The cross-sectional intensity may have a sinusoidal variation, a Gaussian profile, or any other function for cross-sectional intensity.

The local coordinate system XY of the camera 206 may be further characterized by a coordinate system XYZ, where the XY coordinate system defined by the camera include axis Z, which is substantially perpendicular to both the X-axis and the Y-axis. The axis Z includes a range of values for Z based on optics limitations. The values for Z may be based on distances $d_1$ and $d_2$ such that $d_1 \leq z \leq d_2$. A single point from a projected line incident on a plane perpendicular to Z will appear to be displaced in the X direction by $\Delta X$. Based on a triangulation angle, the following condition exists:

$$\Delta z = \frac{\Delta x}{\tan \theta} \quad (2)$$

In a projected line pattern having multiple lines $L_1$-$L_n$, a given line $L_i$ may be characterized by a unique function θ(x). For a given line $L_i$, the location of line $L_i$ with respect to the coordinate system XYZ of the camera 206 for various values of z where $d_1 \leq z \leq d_2$ may be determined through calibration or similar process.

For an observed line $L_c$, a closest calibrated line position may be selected, and the x and z coordinates ($x_c$, $z_c$) of the calibrated line determined. The camera 206 may observe multiple lines during projected on an object 102. For each observed point on the line, as captured or observed by the camera 206, the XY coordinates of that surface point may be directly observed as ($x_{observed}$, $y_{observed}$). A point $z_{observed}$ may be determined by observing the displaced $\Delta x$ (where $\Delta x = x_{observed} - x_c$), to compute $\Delta z$. The z coordinate may then be computed as:

$$z_{observed} = z_c + \Delta z. \quad (3)$$

The maximum displacement for any line in the volume may be determined by:

$$\Delta x = (d_1 - d_2) \tan \theta \quad (4)$$

A maximum number of simultaneously distinguishable lines $n_{max}$ may be determined as:

$$n_{max} = \frac{X_{max}}{(d_1 - d_2) \tan \theta_{max}} \quad (4)$$

The maximum number of simultaneously distinguishable lines $n_{max}$ increases with a decreasing depth of field $d_1$-$d_2$. The maximum number of simultaneously distinguishable lines $n_{max}$ also increases with as $\theta_{max}$ decreases. The accuracy of the determination also may also decrease with smaller $\theta_{max}$ values. Also, decreasing a depth of field may result in a less useful volume for digitizing.

Figure 3:
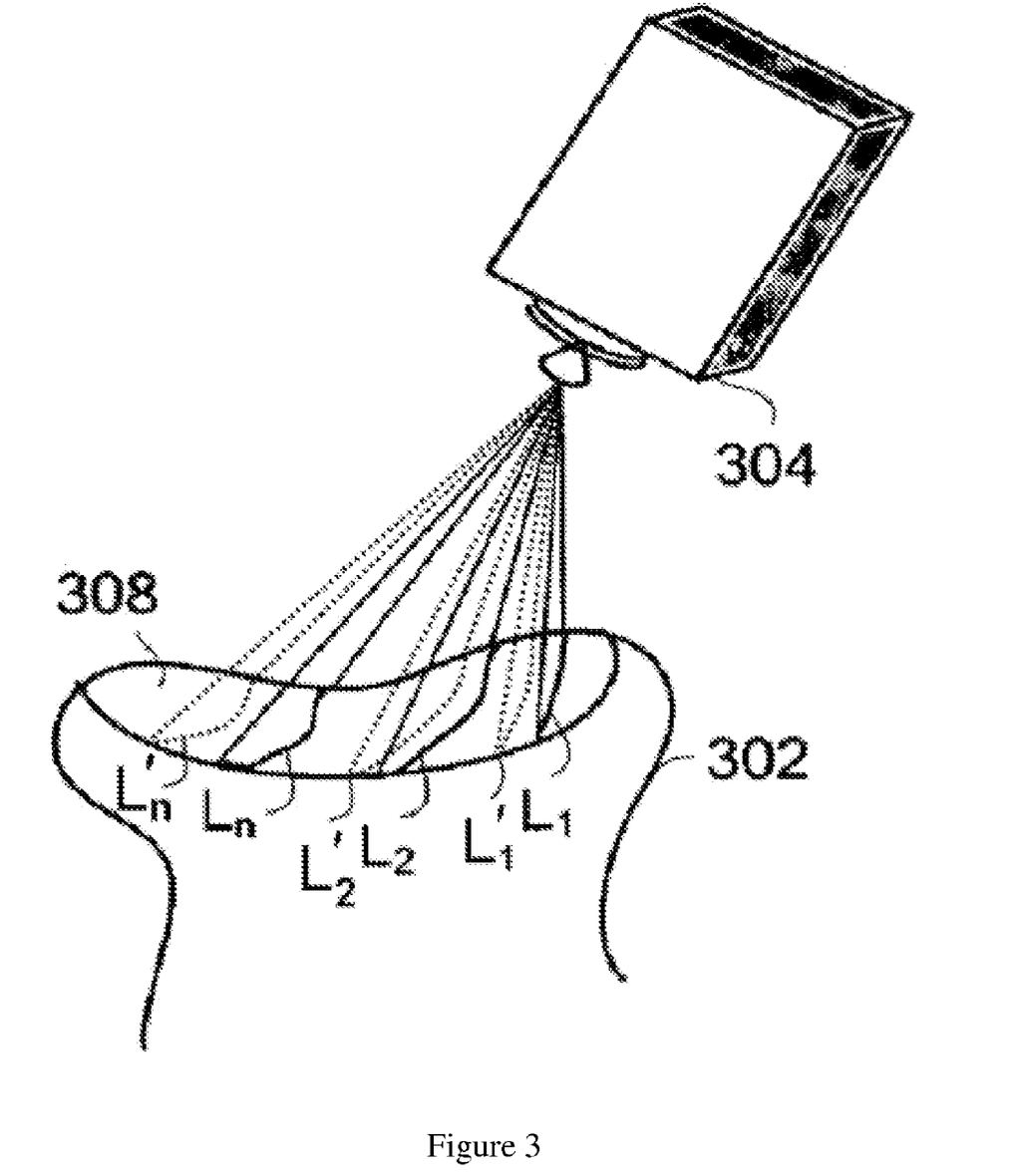
FIG. 3 illustrates a line pattern incident on a surface of an object.

FIG. 3 illustrates a line pattern having multiple lines $L_1$-$L_n$ projected toward an object 302. Each line $L_1$-$L_n$ represents a connected series of points or curvilinear segments where a normal vector n at any point along the curve obeys equation 1 above. The multiple lines $L_1$-$L_n$ are projected toward and incident onto a surface 308 of the object 302.

Multiple patterns of lines $L_1$-$L_n$ may be projected toward the object 302 during a capture period. The light patterns may be referred to as $A_i$ where I=1, 2, ... x, where the first light pattern having $L_1$-$L_n$ lines is referred to as $A_1$ and subsequent line patterns are referred to as $A_2$ to $A_x$. The number of lines n in pattern $A_i$ may be selected so that $n \leq n_{max}$. In FIG. 3, a first pattern includes a number of distinguishable curvilinear lines {$L_1$, $L_2$ and $L_n$}, and a second, subsequent pattern includes a number of distinguishable curvilinear lines {$L'_1$, $L'_2$ and $L'_n$}.

According to Equation (4), each line in pattern $A_1$ incident on the surface 308 may be uniquely labeled or identified. For each line pattern $A_1$, the x, y and z coordinates may be determined for each point on the line using the above equations. For each line $L_i$, data-points representative of characteristics of the surface 308 along the line $L_i$ may be generated. From the data points, a three-dimensional representation of the surface 302 along the line $L_i$ is formed. From all the lines of pattern $A_1$, an approximation of the surface of the object being digitized may be determined.

For the subsequent patterns $A_i$, where i=2, ... x, let $n_i$ represent the number of lines for the pattern $A_i$. For i<j the condition $n_i \leq n_j$ holds. Also, $n_i > n_{max}$ for each i. Because equation (4) no longer holds, labeling or identifying lines for $A_i$ may be resolved during a prior calibration step.

In a calibration step, each line in $A_i$ is characterized on a flat plane for different Z values. Based on the characterization, and an approximation surface, the approximate locations of each labeled line in $A_i$ is estimated by intersecting a known light plane corresponding with each labeled line with the approximation surface 308. The estimation may be compared to the observed line pattern for $A_i$ incident on the surface 302, and observed lines accordingly labeled.

Figure 4:
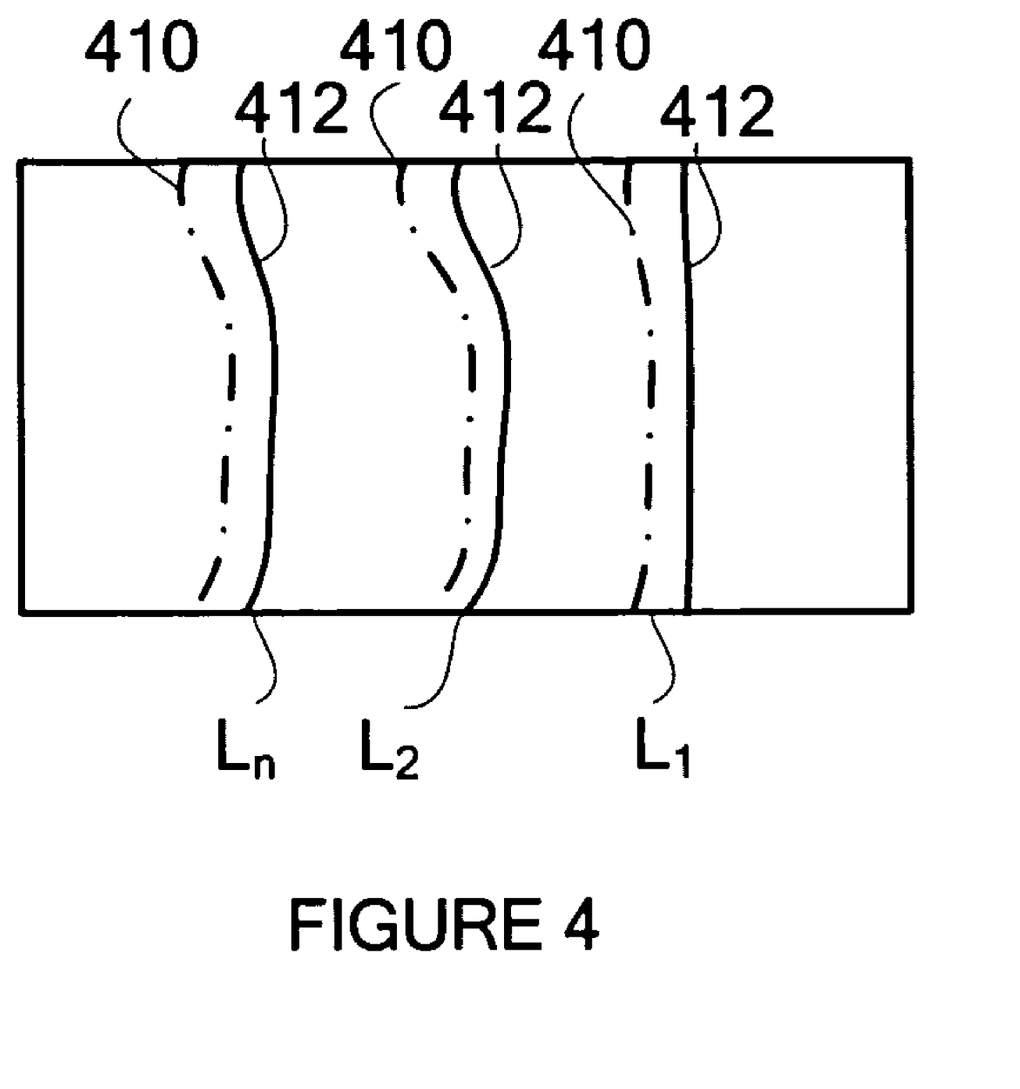
FIG. 4 illustrates an approximate line pattern estimated from a first pattern frame scan for comparison with an actual line pattern for a subsequent frame as observed by the camera of FIG. 1.

FIG. 4 illustrates an approximate line pattern estimated from a first pattern frame scan 410 compared with an actual line pattern 412 for a subsequent frame as observed by camera 206. By choosing closest curves, a unique labeling of the multiple lines $L_1$-$L_n$ is obtained. A new approximation surface is thus obtained by repeated application of equation (4) on each labeled line. This may be repeated using a new and enhanced approximation surface of the surface and a higher density line pattern.

Figure 5:
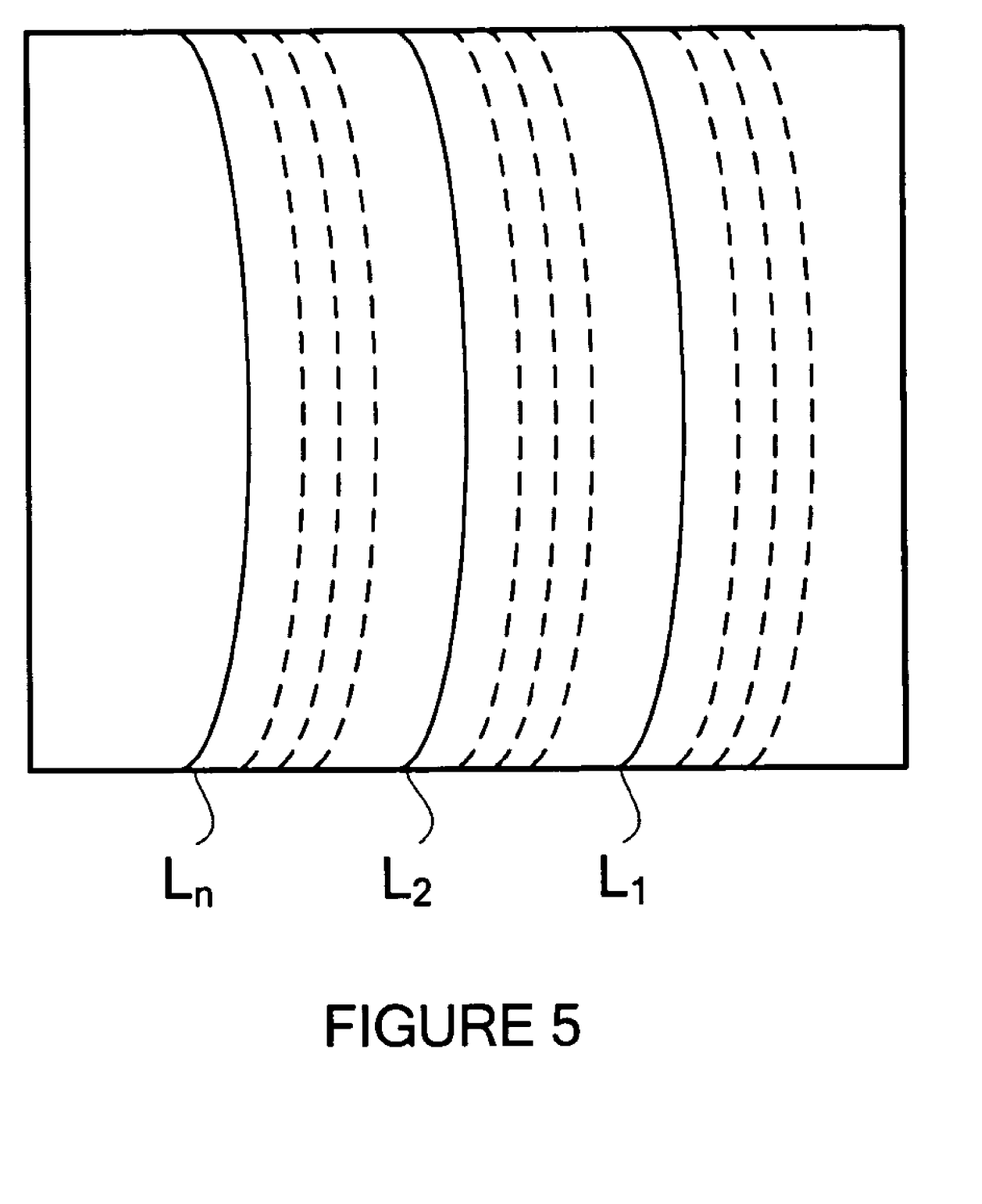
FIG. 5 illustrates non-rectangular regions of distinguishability.

FIG. 5 illustrates non-rectangular regions of distinguishability. In an embodiment, non-rectangular regions of distinguishability may be defined as areas between adjacent projection lines $L_1$-$L_n$. For example, a non-rectangular region of distinguishability may be defined as the region between a first line $L_1$ of the multiple line pattern and a second line $L_2$ of the light pattern. For each line that may be projected onto a planar surface placed at z values between $d_1$ and $d_2$, the region of distinguishability defines the smallest envelope that always includes that line as imaged by the imaging system. Other lines $L_i$ will have separate regions of distinguishability. Therefore, in the exemplary embodiment, each line may be projected to a discrete area where substantially no overlap exists between adjacent areas.

FIG. 5 illustrates an example of a pattern where three lines are being projected, with non-overlapping regions of distinguishability. By allowing non-rectangular regions of distinguishability, the limitations of equation (4) may be minimized or eliminated altogether by allowing non-rectangular regions for each line, where the non-rectangular regions may be compressed without substantial overlap or ambiguity. The number of simultaneous projected lines may be increased by allowing the distinguishable regions around each line to follow a shape of the line instead of a defined rectangular area. Accordingly, the maximum number of simultaneous lines may be increased.

An embodiment for a projector for a high speed multiple line three-dimensional digitization system may include a modulated laser source having a two-axis orthogonal mirror scanner. The scanner may have a single two axis mirror, two orthogonally mounted single axis mirrors, or the equivalents. The scanner may project a two-dimensional light pattern having multiple lines $L_1$-$L_n$ through optics toward a surface of an object. The light pattern illuminates the surface. Light reflected from the surface may be captured by a camera. The patterns incident on the object may be viewed through additional optics, a CCD, CMOS digital camera, or similar device. The line patterns are analyzed and converted to three-dimensional coordinates representative of the illuminated surface.

Figure 6:
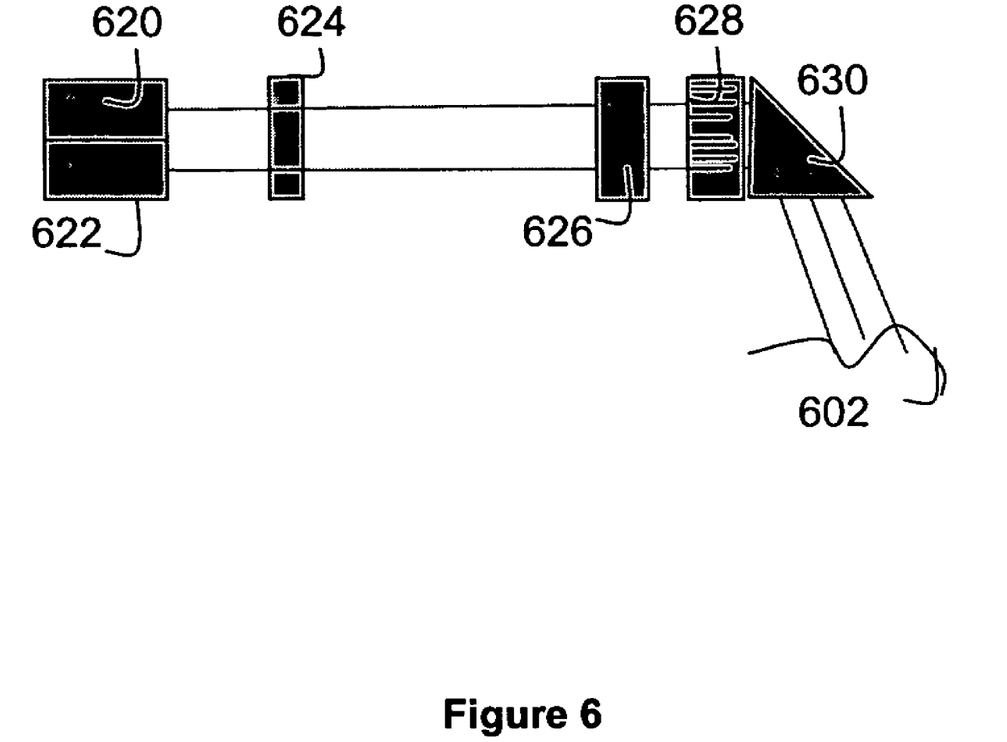
FIG. 6 illustrates an embodiment where multiple light sources are derived from a single laser source switched with a liquid crystal cell.

Referring to FIG. 6, an embodiment having two laser sources 620, 622 is shown. The two laser sources 620, 622 each project a laser beam. The laser beams pass through a focusing lens 624 and a line lens 626 that transforms the single point from each laser source 620, 622 into a line. Each line then passes through two different diffraction gratings 628 that split the line into multiple substantially parallel lines. The multiple minimal patterns may be produced without substantial moving parts.

Figure 7:
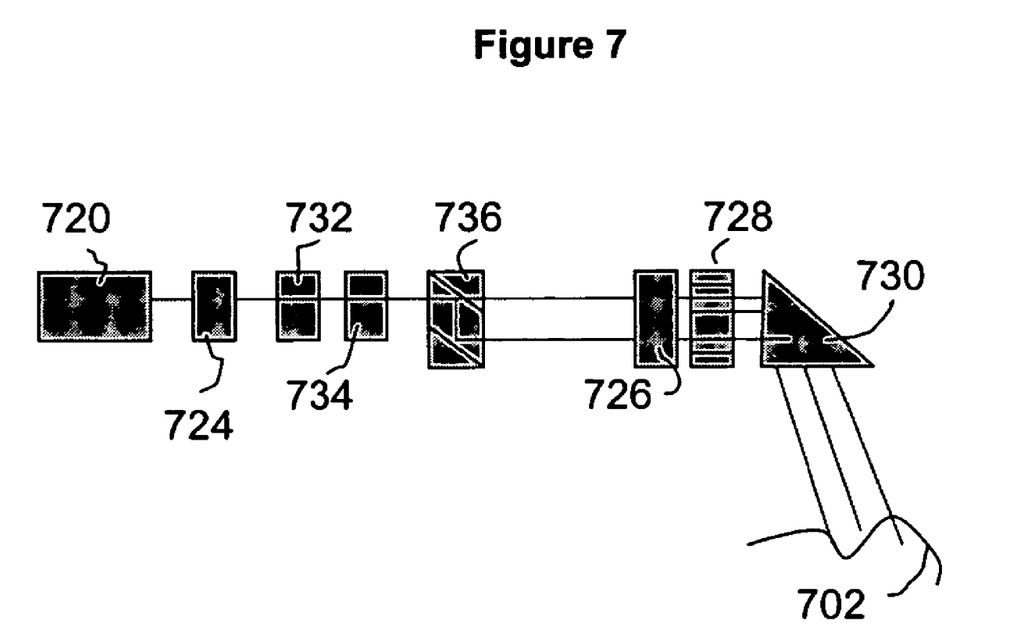
FIG. 7 illustrates an embodiment for multiple laser sources.

Referring to FIG. 7, an embodiment having a single laser source 720 is shown. The laser source 720 may be switched using a liquid crystal (LC) cell 734. The laser light beam from the single laser source 720 passes through a wave plate 732 to polarize the light. The wave plate 732 may be a ½ wave plate. The laser light is polarized based on the LC cell 734, in a particular direction and/or orientation, where the direction may be switched by switching the LC cell 734. Two possible paths for the light may pass through the beam splitter 736 so that the single laser beam may be split to two paths. The laser point may be processed as described.

In an embodiment for a high speed multiple line three-dimensional digitization system, a scanner and camera may be configured as described according to co-pending U.S. patent application Ser. No. 10/749,579, entitled LASER DIGITIZER SYSTEM FOR DENTAL APPLICATIONS, filed on Dec. 30, 2003, the description of which is incorporated herein in its entirety. The scanner may be a modulated laser source, coupled to a two axis orthogonal mirror scanner. An embodiment for a high speed multiple line three-dimensional digitization system may include a modulated laser source, coupled to a two axis orthogonal mirror scanner. The scanner may have a single two axis mirror, two orthogonally mounted single axis mirrors, or the equivalents. By varying the rotation of the mirror(s), and by modulating the laser beam, a two-dimensional pattern may be traced. The pattern may be projected through optics onto the physical object, and the patterns incident on the object viewed through additional optics, a CCD, CMOS digital camera, or similar device. The line patterns are analyzed and converted to three-dimensional coordinates for the surface.

It is intended in the appended claims to cover all such changes and modifications which fall within the true spirit and scope of the invention. Therefore, the invention is not limited to the specific details, representative embodiments, and illustrated examples in this description. Accordingly, the invention is not to be restricted except in light as necessitated by the accompanying claims and their equivalents.

What is claimed is:

1. A method for digitizing a physical object, comprising:
   (a) projecting a plurality of sequential light patterns onto a surface of an object, where each of the plurality of sequential patterns includes a plurality of distinguishable curvilinear lines, where a first pattern includes a first number of distinguishable curvilinear lines, and a subsequent pattern includes at least the same number of lines than the first number of distinguishable curvilinear lines;
   (b) capturing light reflected from the surface;
   (c) determining coordinates x, y, z of points on the surface according to the captured light; and
   (d) using the coordinates to generate a representation of the physical object.

2. The method of claim 1 where the plurality of sequential patterns comprises white light.

3. The method of claim 1 where each of the plurality of distinguishable curvilinear lines is characterized by an intensity profile being substantially constant over time.

4. The method of claim 1 where step (a) further comprises generating a light pattern according to tracing a laser point with a two axis mirror to generate the plurality of distinguishable curvilinear lines.

5. The method of claim 4 where each of plurality of distinguishable curvilinear lines is characterized by a modulated intensity pattern.

6. The method of claim 1 where step (a) further comprises generating a light pattern according to tracing a laser point with a plurality of orthogonally mounted single axis mirrors to generate the plurality of distinguishable curvilinear lines.

7. The method of claim 1 further comprising optically generating the plurality of distinguishable curvilinear lines.

8. The method of claim 7 where each of the plurality of distinguishable curvilinear lines is characterized by a modulated intensity pattern and a scan speed.

9. The method of claim 8 where the scan speed and modulation are variable.

10. The method of claim 1 further comprising optically projecting multiple laser points through a plurality of optical elements to generate a plurality of static patterns of illuminated lines.

11. The method of claim 10 further comprising a single laser source to generate the plurality of distinguishable curvilinear lines.

12. The method of claim 11 further comprising producing the plurality of distinguishable curvilinear lines using a mechanical switch.

13. The method of claim 12 where the mechanical switch comprises a mirror.

14. The method of claim 13 where the plurality of distinguishable curvilinear lines are produced using an electro-optical switch.

15. The method of claim 14 where the electro-optical switch comprises an LC switch.

16. The method of claim 1 further comprising processing the coordinates in a computer system.

17. The method of claim 1 where the subsequent pattern includes a greater number of lines than the first number of distinguishable curvilinear lines.

18. The method of claim 1 further comprising displaying the coordinates as a visual representation of the surface.

19. A dental imaging system, comprising:
 (a) means for projecting a plurality of sequential patterns toward a dental item, each of the plurality of sequential patterns including a plurality of distinguishable curvilinear lines, where a first pattern includes a first number of distinguishable curvilinear lines, and a subsequent pattern includes a second number of distinguishable curvilinear lines, wherein within a pattern each curvilinear line is associated with a region that is non-rectangular and that does not overlap with a region associated with an adjacent curvilinear line;
 (b) means for capturing light reflected from a surface of the dental item;
 (c) means for determining data points associated with characteristics of the surface according to the captured light reflected from the surface; and
 (d) means for displaying the a three-dimensional representation of the surface of the dental item according to the data points.

20. A dental digitizing system, comprising:
 (a) a projector configured to illuminate a dental object during each of sequence of exposure periods with a light patterns including a plurality of distinguishable curvilinear lines, where a first light pattern includes a first number of distinguishable curvilinear lines, and a subsequent light pattern includes a second number of distinguishable curvilinear lines, wherein within a pattern each curvilinear line is associated with a region that is non-rectangular and that does not overlap with a region associated with an adjacent curvilinear line;
 (b) a camera configured to capture an image according to light reflected during each exposure period;
 (c) a controller configured to determine a set of points associated with characteristics of a surface of the object according to each image, and to compile each of the captured images to form an image of the object; and
 (d) a display for displaying the image of the object.

21. The dental digitizing of claim 20 where the projector comprises a laser source configured to optically generate the plurality of distinguishable curvilinear lines from a single point laser source.

22. The dental digitizing of claim 20 where the projector comprises a plurality of laser sources configured to generate the plurality of distinguishable curvilinear lines.

* * * * *